(12) United States Patent
Shalyaev et al.

(10) Patent No.: US 6,566,295 B2
(45) Date of Patent: May 20, 2003

(54) METHOD AND CATALYST SYSTEM FOR PRODUCING AROMATIC CARBONATES

(75) Inventors: Kirill Vladimirovich Shalyaev, Clifton Park; Grigorii Lev Soloveichik, Latham; Bruce Fletcher Johnson, Scotia, all of NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/728,224

(22) Filed: Nov. 30, 2000

(65) Prior Publication Data

US 2002/0099235 A1 Jul. 25, 2002

(51) Int. Cl.$^7$ ................................. B01J 31/00
(52) U.S. Cl. ................. 502/150; 502/162; 502/165; 502/167; 502/224; 502/225; 502/227; 502/229; 502/230
(58) Field of Search ................ 502/150, 162, 502/165, 167, 224, 225, 227, 229, 230

(56) References Cited

U.S. PATENT DOCUMENTS

| | | |
|---|---|---|
| 4,187,242 A | 2/1980 | Chalk |
| 5,231,210 A | 7/1993 | Joyce et al. |
| 5,239,106 A | 8/1993 | Shafer |
| 5,284,964 A | 2/1994 | Pressman et al. |
| 5,373,083 A | 12/1994 | King et al. |
| 5,380,907 A | 1/1995 | Mizukami et al. |
| 5,399,734 A | 3/1995 | King et al. |
| 5,498,789 A | 3/1996 | Takagi et al. |
| 5,502,232 A | 3/1996 | Buysch et al. |
| 5,543,547 A | 8/1996 | Iwane et al. |
| 5,625,091 A | 4/1997 | Buysch et al. |
| 5,663,408 A | 9/1997 | Buysch et al. |
| 5,726,340 A | 3/1998 | Takagi et al. |
| 5,760,272 A | 6/1998 | Pressman et al. |
| 5,821,377 A | 10/1998 | Buysch et al. |
| 5,856,554 A | 1/1999 | Buysch et al. |
| 6,114,564 A | 9/2000 | Pressman et al. |
| 6,143,913 A | 11/2000 | Spivack et al. |
| 6,172,254 B1 | 1/2001 | Pressman et al. |
| 6,180,812 B1 | 1/2001 | Johnson et al. |
| 6,215,014 B1 * | 4/2001 | Johnson et al. ............. 502/325 |
| 6,323,358 B1 * | 11/2001 | Patel et al. ................. 502/102 |

FOREIGN PATENT DOCUMENTS

| | | |
|---|---|---|
| EP | 071286 | 2/1983 |
| EP | 736325 | 3/1996 |
| GB | 1102566 | 2/1968 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |
| JP | 10-158221 | 6/1998 |
| JP | 10-316627 | 12/1998 |
| WO | WO 00/66530 | 11/2000 |
| WO | WO 00/66534 | 11/2000 |
| WO | WO 00/66535 | 11/2000 |

OTHER PUBLICATIONS

International Search Report for PCT/US01/50668 Mailed May 2002.

* cited by examiner

Primary Examiner—Elizabeth D. Wood
(74) Attorney, Agent, or Firm—S. Brube Brown; Noreen C. Johnson

(57) ABSTRACT

A method and catalyst system for economically producing aromatic carbonates from aromatic hydroxy compounds is disclosed. In one embodiment, the present invention provides a method of carbonylating aromatic hydroxy compounds by contacting at least one aromatic hydroxy compound with oxygen and carbon monoxide in the presence of a carbonylation catalyst system that includes an effective amount of at least one Group 8, 9, or 10 metal source; an effective amount of at least one bromide composition; an effective amount of at least one activating organic solvent; an effective amount of a combination of inorganic co-catalysts comprising at least one titanium source and at least one copper source; and an effective amount of at least one base.

30 Claims, No Drawings

METHOD AND CATALYST SYSTEM FOR PRODUCING AROMATIC CARBONATES

BACKGROUND OF THE INVENTION

The present invention is directed to a method and catalyst system for producing aromatic carbonates and, more specifically, to a method and catalyst system for producing diaryl carbonates through the carbonylation of aromatic hydroxy compounds.

Aromatic carbonates find utility, inter alia, as intermediates in the preparation of polycarbonates. For example, a popular method of polycarbonate preparation is the melt transesterification of aromatic carbonates with bisphenols. This method has been shown to be environmentally superior to previously used methods which employed phosgene, a toxic gas, as a reagent and chlorinated aliphatic hydrocarbons, such as methylene chloride, as solvents.

Various methods for preparing aromatic carbonate monomers have been previously described in the literature and/or utilized by industry. A method that has enjoyed substantial popularity in the literature involves the direct carbonylation of aromatic hydroxy compounds with carbon monoxide and oxygen. In general, practitioners have found that the carbonylation reaction requires a rather complex catalyst system. For example, in U.S. Pat. No. 4,187,242, which is assigned to the assignee of the present invention, Chalk reports that a carbonylation catalyst system should contain a Group 8, 9, or 10 metal, such as ruthenium, rhodium, palladium, osmium, iridium, platinum, or a complex thereof. Further refinements to the carbonylation reaction include the identification of organic co-catalysts, such as terpyridines, phenanthrolines, quinolines and isoquinolines in U.S. Pat. No. 5,284,964 and the use of certain halide compounds, such as quaternary ammonium or phosphonium halides in U.S. Pat. No. 5,399,734, both patents also being assigned to the assignee of the present invention.

The economics of the carbonylation process are strongly dependent, inter alia, on the number of moles of aromatic carbonate produced per mole of Group 8, 9, or 10 metal utilized (i.e. "catalyst turnover"). Consequently, much work has been directed to the identification of efficacious inorganic co-catalysts that increase catalyst turnover. In U.S. Pat. No. 5,231,210, which is also assigned to General Electric Company, Joyce et al. report the use of a cobalt pentadentate complex as an inorganic co-catalyst ("IOCC"). In U.S. Pat. No. 5,498,789, Takagi et al. report the use of lead as an IOCC. In U.S. Pat. No. 5,543,547, Iwane et al. report the use of trivalent cerium as an IOCC. In U.S. Pat. No. 5,726,340, Takagi et al. report the use of lead and cobalt as a binary IOCC system. In co-pending application Ser. No. 09/677,487, filed Oct. 2, 2000, Soloveichik et al. report the use of lead and copper as a binary IOCC system.

Further complexity was added to carbonylation catalyst systems by Buysch et al. in U.S. Pat. No. 5,502,232, which teaches the use of a quaternary salt, a co-catalyst, a base, and a desiccant in a supported Pd-based carbonylation system. In U.S. Pat. No. 5,821,377, Buysch et al. report the use of said aforementioned catalyst system with the Pd and the co-catalyst provided on the same support.

The literature is virtually silent, however, as to the role of various catalyst system components, such as IOCCs and onium halides for example, in the carbonylation reaction (i.e., the reaction mechanism). Accordingly, meaningful guidance regarding the identification of additional catalyst systems is cursory at best. It would be desirable to identify catalyst systems that would minimize consumption of costly components (e.g., palladium and onium halides) or perhaps that would omit these components. It would also be desirable to minimize the aforementioned consumption of costly components while increasing selectivity toward desirable products and minimizing formation of undesirable byproducts (e.g., 2- and 4-bromophenols). Unfortunately, due to the lack of guidance in the literature, the identification of effective carbonylation catalyst systems has become a serendipitous exercise.

As the demand for high performance plastics continues to grow, new and improved methods of providing product more economically are needed to supply the market. In this context, various processes and catalyst systems are constantly being evaluated; however, the identities of improved and/or additional effective catalyst systems for these processes continue to elude the industry. Consequently, a long felt, yet unsatisfied need exists for new and improved methods and catalyst systems for producing aromatic carbonates and the like.

SUMMARY OF THE INVENTION

Accordingly, the present invention is directed to a method and catalyst system for producing aromatic carbonates. In one embodiment, the present invention provides a carbonylation catalyst system comprising an effective amount of at least one Group 8, 9, or 10 metal source; an effective amount of at least one bromide composition; an effective amount of at least one activating organic solvent; an effective amount of a combination of inorganic co-catalysts comprising at least one titanium source and at least one copper source; and an effective amount of at least one base.

In another embodiment, the present invention provides a method for carbonylating aromatic hydroxy compounds, said method comprising the step of: contacting at least one aromatic hydroxy compound with oxygen and carbon monoxide in the presence of a carbonylation catalyst system comprising an effective amount of at least one Group 8, 9, or 10 metal source; an effective amount of at least one bromide composition; an effective amount of at least one activating organic solvent; an effective amount of a combination of inorganic co catalysts comprising at least one titanium source and at least one copper source; and an effective amount of at least one base.

Various features, aspects, and advantages of the present invention will become more apparent with reference to the following description and appended claims.

DETAILED DESCRIPTION OF PREFERRED EMBODIMENTS

The present invention is directed to a method and catalyst system for producing aromatic carbonates. In one embodiment, the method includes the step of contacting at least one aromatic hydroxy compound with oxygen and carbon monoxide in the presence of a carbonylation catalyst system that comprises an effective amount of a Group 8, 9, or 10 metal source; an effective amount of a bromide composition; an effective amount of an activating organic solvent; an effective amount of a combination of inorganic co-catalysts comprising a titanium source and a copper source; and an effective amount of a base.

Unless otherwise noted, the term "effective amount," as used herein, includes that amount of a substance capable of either increasing (directly or indirectly) the yield of the carbonylation product or increasing selectivity toward an aromatic carbonate. Optimum amounts of a given substance can vary based on reaction conditions and the identity of other constituents yet can be readily determined in light of the discrete circumstances of a given application.

Aromatic hydroxy compounds which may be used in the practice of the present invention include aromatic mono or polyhydroxy compounds, such as phenol, cresol, xylenol, resorcinol, hydroquinone, and bisphenol A. Aromatic organic mono hydroxy compounds are preferred, with phenol being more preferred.

Any aromatic hydroxy compound convertible to a carbonate ester may be employed in the present invention. Suitable aromatic hydroxy compounds include monocyclic, polycyclic or fused polycyclic aromatic monohydroxy or polyhydroxy compounds having from 6 to 30, and preferably from 6 to 15 carbon atoms. Illustrative examples include mono- and poly-hydroxy compounds such as phenol, alkylphenols, o-, m- or p-cresol, o-, m- or p-chlorophenol, o-, m- or p-ethylphenol, o-, m- or p-propylphenol, o-, m- or p-methoxyphenol, methyl salicylate, 2,6-dimethylphenol, 2,4-dimethylphenol, 3,4-dimethylphenol, 1 naphthol and 2-naphthol, xylenol, resorcinol, hydroquinone, catechol, cumenol, the various isomers of dihydroxynaphthalene, bis(4-hydroxyphenyl) propane-2,2, $\alpha,\alpha'$-bis(4-hydroxyphenyl)-p-diisopropylbenzene, and bisphenol A. Aromatic monohydroxy compounds are particularly preferred with phenol being the most preferred. In the case of substituents on the aromatic hydroxy compound, the substituents are generally 1 or 2 substituents and are preferably from C-1 to C-4 alkyl, C-1 to C-4 alkoxy, fluorine, chlorine or bromine.

When an aromatic hydroxy compound as a raw material is used as a reaction solvent, then another solvent need not be used. However, the reaction mixture may also optionally contain at least one relatively inert solvent, that is a solvent whose presence does not substantially improve the yield of or selectivity toward the aromatic carbonate. Illustrative inert solvents include, but are not limited to, hexane, heptane, cyclohexane, methylene chloride, or chloroform.

In various preferred embodiments, the carbonylation catalyst system contains at least one constituent from the Group 8, 9, or 10 metals or a compound thereof. A preferred Group 8, 9, or 10 constituent is an effective amount of a palladium source. In various embodiments, the palladium source may be in elemental form, or it may be employed as a palladium compound. The palladium material can be employed in a form that is substantially soluble in the reaction media or in a form which is substantially insoluble in the reaction media, such as a supported- or polymer-bound palladium species. Accordingly, palladium black or palladium deposited on carbon, palladium deposited on alumina or palladium deposited on silica may be used as well as palladium halides, palladium chloride, palladium bromide, palladium iodide; palladium sulfate; palladium nitrate, palladium carboxylates, palladium oxides, palladium acetate and palladium 2,4-pentanedionate; and paladium complexes containing carbon monoxide, amines, nitrites, phosphines or olefins. As used herein, the term "complexes" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes.

In various applications, it may be preferable to utilize palladium(II) salts of organic acids, including carboxylates with $C_{2-6}$ aliphatic carboxylic acids and palladium(II) salts of β-diketones. Palladium(II) acetate and palladium(II) 2,4-pentanedionate (also know as palladium(II) acetylacetonate) are generally most preferred. Mixtures of palladium materials are also contemplated.

The quantity of the at least one Group 8, 9, or 10 metal catalyst is not particularly limited in the process of the present invention. Preferably, the amount of Group 8, 9, or 10 metal source employed should be sufficient to provide about 1 mole of metal per 800–1,000,000 moles of aromatic hydroxy compound, more preferably per 4000–1,000,000 moles of aromatic hydroxy compound, still more preferably per 40,000–200,000 moles of aromatic hydroxy compound, and yet still more preferably per 65,000–100,000 moles of aromatic hydroxy compound.

The carbonylation catalyst system further contains an effective amount of at least one bromide composition, such as an organic bromice salt. The salt may be an onium salt such as a sulfonium or quaternary ammonium or phosphonium salt, or a guanidinium salt. Illustrative examples of guanidinium salts include, but are not limited to, hexasubstituted guanidinium salts, such as hexaalkyl guanidinium bromides, hexaaryl guanidinium bromides, and hexasubstituted guanidinium bromides containing mixtures of alkyl and aryl substituents each substituent group independently having a carbon number of 1 to 22. In various embodiments, $\alpha,\omega$-bis(pentaalkylguanidinium)alkane salts may be preferred.

Organic residues on the onium salts are typically include $C_{6-10}$ aryl, $C_{7-12}$ aralkyl, or $C_{1-20}$ alkyl, or combinations thereof. Illustrative examples of onium salts include, but are not limited to, tetraalkylammonium or tetraalkylphosphonium bromides. Preferred onium salts are alkyl ammonium bromides containing primary and/or secondary alkyl groups containing about 1–8 carbon atoms. Particularly preferred organic bromide compositions include tetrabutylammonium bromide, tetraethylammonium bromide, and hexaethylguanidinium bromide.

In preferred embodiments, the bromide composition can be chosen from various alkali metal bromide salts. Accordingly, a non-exclusive listing of preferred alkali metal bromide salts includes lithium bromide, sodium bromide, potassium bromide, and cesium bromide. Mixtures of the aforementioned salts are also suitable for use in the invention.

In preferred embodiments, the carbonylation catalyst system can contain between about 1 and about 2000 moles of bromide per mole of Group 8, 9, or 10 metal employed. More preferably, between about 2 and about 1500, and still more preferably between about 5 and about 1000 moles of bromide are used per mole of Group 8, 9, or 10 metal employed.

The carbonylation catalyst system includes an effective amount of at least one activating organic solvent. Preferred activating organic solvents include polyethers; i.e., compounds containing two or more C—O—C linkages. The polyether used is preferably free from hydroxy groups to maximize its desired activity and avoid competition with the aromatic hydroxy compound in the carbonylation reaction. Preferred polyethers contain two or more (O—C—C) units.

The polyether may be aliphatic or mixed aliphatic-aromatic. As used in the identification of the polyether, the term "aliphatic" refers to the structures of hydrocarbon groups within the molecule, not to the overall structure of the molecule. Thus, "aliphatic polyether" includes heterocyclic polyether molecules containing aliphatic groups within their molecular structure. Suitable liphatic polyethers include diethylene glycol dialkyl ethers such as diethylene glycol dimethyl ether (hereinafter "diglyme"), triethylene glycol dialkyl ethers such as triethylene glycol dimethyl ether (hereinafter "triglyme"), tetraethylene glycol dialkyl ethers such as tetraethylene glycol dimethyl ether (hereinafter "tetraglyme"), polyethylene glycol dialkyl ethers such as polyethylene glycol dimethyl ether and crown ethers such as 15-crown-5(1,4,7,10,13-pentaoxacyclopentadecane) and 18-crown-6(1,4,7,10,13,16-hexaoxacyclooctadecane). Illustrative mixed aliphatic-aromatic polyethers include diethylene glycol diphenyl ether and benzo-18-crown-6.

In alternative embodiments, the activating organic solvent can be a nitrile. Suitable nitrile promoters for the present method include $C_{2-8}$ aliphatic or $C_{7-10}$ aromatic mono- or dinitriles. Illustrative mononitriles include acetonitrile, propionitrile, and benzonitrile. Illustrative dinitriles include succinonitrile, adiponitrile, and benzodinitrile. Mononitriles are generally preferred; more specifically preferred is acetonitrile. It is noted that the function of the nitrile promoter in the present method is not that of an inert solvent. Rather, the nitrile is an active catalyst component that improves the yield of or selectivity toward the aromatic carbonate.

In further alternative embodiments, the activating organic solvent can be a carboxylic acid amide. Fully substituted amides (containing no NH groups including the amide nitrogen) are preferred. Aliphatic, aromatic or heterocyclic amides may be used. Illustrative amides are dimethylformamide, dimethylacetamide (hereinafter sometimes "DMA"), dimethylbenzamide and N-methylpyrrolidinone (NMP). Particularly preferred are NNP and DMA.

The activating organic solvent can be a sulfone, which may be aliphatic, aromatic or heterocyclic. Illustrative sulfones are dimethyl sulfone, diethyl sulfone, diphenyl sulfone and sulfolane (tetrahydrothiophene-1,1-dioxide). Of these, sulfolane is often preferred.

It is noted that the function of the activating organic solvent in the present invention is not that of an inert solvent. Rather, the activating organic solvent is an active catalyst component that improves the yield of or selectivity toward the aromatic carbonate. The role of the activating organic solvent is believed to be to increase the degree of dissociation and ionization of bromide composition, such as sodium bromide, perhaps by forming a complex with the cationic portion of said component, although the invention is in no way dependent on this or any other theory of operation. The amount of activating organic solvent employed will be an amount effective to optimize diaryl carbonate formation, in general by increasing the yield of the desired diaryl carbonate as evidenced, for example, by an increase in "turnover number"; i.e., the number of moles of diaryl carbonate formed per gram-atom of the Group 8, 9, or 10 metal catalyst component present. This amount is most often about 1–60% by volume, preferably about 1–25% by volume, more preferably about 2–15% by volume, still more preferably about 4–12% by volume, and yet still most preferably about 6–8% by volume based on the total of aromatic hydroxy compound and activating organic solvent.

The amount of activating organic solvent may, however, typically depend to some extent on the bromide composition and the complexing ability of the activating organic solvent employed. Crown ethers, for example, have a very high complexing tendency with metal cations. For example, 15-crown-5 complexes efficiently with sodium and 18-crown-6 with potassium. Such compounds may be used in amounts as low as an equimolar amount based on bromide composition. Other compounds useful as activating organic solvent, such as straight chain polyethers (e.g., diglyme), may be optimally effective at much higher levels. The preferred proportion of any specific material used as activating organic solvent can be determined by simple experimentation.

The carbonylation catalyst system includes an effective amount of a combination of inorganic co-catalysts (IOCCs) comprising at least one titanium source and at least one copper source. Additional IOCCs may be used in the carbonylation catalyst system, provided the additional IOCC does not deactivate (i.e. "poison") the original IOCC combination, such that it loses its effectiveness. A non-exclusive listing of additional IOCCs includes lead, cerium, iron, ytterbium, zinc, manganese, europium, bismuth, nickel, cobalt, zirconium, iridium, rhodium, ruthenium, chromium, and yttrium. Suitable IOCCs include elemental metals, metal compounds, and precursors thereof which may form catalytically active metal species under the reaction conditions, it being possible for use to be made of the metal in various degrees of oxidation. IOCCs may be initially soluble in the reaction mixture or initially insoluble as in supported- or polymer-bound IOCC species. Alternatively, IOCCs may be initially insoluble in the reaction mixture and form soluble IOCC species during the course of the reaction.

An IOCC can be introduced to the carbonylation reaction in various forms, including salts and complexes, such as tetradentate, pentadentate, hexadentate, or octadentate complexes. Illustrative forms may include oxides, halides, carboxylates, diketones (including beta-diketones), nitrates, complexes containing carbon monoxide or olefins, and the like. Suitable beta-diketones include, those known in the art as ligands for the IOCC metals of the present invention. Examples include, but are not limited to, acetylacetone, benzoylacetone, dibenzoylmethane, diisobutyrylmethane, 2,2-dimethylheptane-3,5-dione, 2,2,6-trimethylheptaner-3, 5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). An IOCC may be used in its elemental form if sufficient reactive surface area can be provided. In embodiments employing supported palladium, it is noted that the IOCC provides a discrete, catalytic source of metal in a form favorable for such catalysis.

Examples of titanium sources are inorganic titanium salts such as titanium(IV) bromide, titanium (IV) chloride; titanium alkoxides and aryloxides such as titanium (IV) methoxide, titanium (IV) ethoxide, titanium (IV) isopropoxide, titanium (IV) 2-ethylhexoxide, titanium(IV) butoxide, titanium (IV) 2-ethyl-1,3-hexanediolate, titanium (IV) (triethanolaminato)isopropoxide and titanium(IV) phenoxide; and titanium salts of β-diketones or β-ketoesters such as titanium (IV) diisopropoxide bis(acetylacetonate), titanium (IV) bis(ethyl acetoacetato)diisopropoxide, titanium(IV) oxide bis(2,4-pentanedionate) (or titanium (IV) oxide acetylacetonate). Mixtures of titanium compounds may also be employed. The preferred titanium sources are titanium(IV) alkoxides and aryloxides such as titanium (IV) butoxide and titanium (IV) phenoxide; and salts of β-diketones or β-ketoesters such as titanium (IV) oxide acetylacetonate and titanium (IV) bis(ethyl acetoacetato) diisopropoxide.

Examples of copper sources are inorganic cupric or cuprous salts or copper complexes. Illustrative examples include, but are not limited to, copper (I) chloride, copper (I) bromide, copper (I) iodide; copper (II) chloride, copper (II) bromide, copper (II) iodide; copper carboxylates such as copper acetate, copper gluconate, and copper (II) 2-ethylhexanoate; copper (II) hydroxide, copper alkoxides and aryloxides; copper nitrate; and copper salts of β-diketones such as copper (II) bis(2,4-pentanedionate) (or copper (II) acetylacetonate). Mixtures of copper compounds may also be employed. The preferred copper sources are 2,4-pentanedionates.

IOCCs are included in the carbonylation catalyst system in effective amounts. In this context an "effective amount" is an amount of IOCC (or combination of IOCCs) that increases the number of moles of aromatic carbonate produced per mole of Group 8, 9, or 10 metal utilized; increases the number of moles of aromatic carbonate produced per mole of bromide utilized; or increases selectivity toward aromatic carbonate production beyond that obtained in the absence of the IOCC (or combination of IOCCs). Optimum amounts of an IOCC in a given application will depend on various factors, such as the identity of reactants and reaction conditions. Typically, at least one IOCC is present in the amount of about 0.2–200 gram-atoms of metal, preferably about 1–150 gram-atoms of metal, and more preferably about 2–100 gram-atoms of metal per gram-atom of the Group 8, 9, or 10 metal. For example, when palladium is included in the reaction, the molar ratio of titanium relative to palladium at the initiation of the reaction is preferably between about 0.1 and about 150, and the molar ratio of copper relative to palladium is preferably between about 0.1 and about 15. In preferred embodiments the mole ratio of copper to titanium is about 5–20 moles copper to 2–30 moles titanium.

The carbonylation catalyst system also includes an effective amount of at least one base. In this context, the term "effective amount" carries the same definition as it does relative to IOCCs. Any desired bases or mixtures thereof, whether organic or inorganic may be used. Illustrative examples of inorganic bases include, but are not limited to, alkali metal hydroxides and alkali metal carbonates, alkali metal carboxylates or other salts of weak acids or alkali metal salts of aromatic hydroxy compounds, for example alkali metal phenoxidels. Obviously, the hydrates of alkali metal phenoxides can also be used in the process. An example of such a hydrate which may be mentioned is sodium phenoxide trihydrate1 However, the amount of water added must preferably be measured in such a way that, per mol base, at most 5 moles of water are added. Higher water concentrations lead, inter alia, to poorer conversion rates and decomposition of carbonates formed. Illustrative examples of organic bases include, but are not limited to, onium hydroxides, onium phenoxides, ammonium hydroxides, ammonium phenoxides, phosphonium hydroxides, phosphonium phenoxides, sulfonium hydroxides, sulfonium phenoxides, guanidinium hydroxides, guanidinium phenoxides, tertiary amines which bear as organic radicals $C_6$–$C_{10}$ aryl, $C_6$–$C_{12}$ aralkyl and/or $C_1$–$C_{20}$-alkyl or represent pyridine bases or hydrogenated pyridine bases; for example dimethylbutylamine, triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxy compound, particularly preferably an alkali metal salt of the aromatic hydroxy compound which is also to be converted to the organic carbonate. These alkali metal salts can be lithium salts, sodium salts, potassium salts, rubidium salts or cesium salts. Lithium phenoxide, sodium phenoxide and potassium phenoxide are preferably used; sodium phenoxide is particularly preferred.

A base may be added as a pure compound or as a precursor compound, such as addition of an alkali metal-comprising base as a precursor for an alkali metal salt of the aromatic hydroxy compound which is also to be converted to the organic carbonate. Illustrative alkali metal-comprising bases include, but are not limited to, sodium hydroxide, and sodium salts of weak acids such as sodium carboxylates, sodium acetate, and sodium acetylacetonate. A base may be added to the reaction mixture in any convenient form, such as in solid form or as a liquid or a melt, either in neat form or in a solution. In a further embodiment of the invention, the base is added to the reaction mixture as a solution which contains about 0.1 to about 80% by weight, preferably about 0.5 to about 65% by weight, particularly preferably about 1 to about 50% by weight of the base. The solvents which may optionally be used here are both alcohols or phenols, such as the phenol to be reacted, and inert solvents. Examples of solvents which may be mentioned are dimethylacetamide, N-methylpyrrolidinone, dioxane, t-butanol, cumyl alcohol, isoamyl alcohol, tetramethylurea, diethylene glycol, halogenated hydrocarbons (e.g. chlorobenzene or dichlorobenzene) and ethers, such as tetraethylene glycol dimethyl ether. The solvents may be used alone or in any combination with each other. In preferred embodiments, between about 0.1 and about 2500 molar equivalents of base are employed (relative to Group 8, 9, or 10 metal). More preferably, between about 5 and about 1500 molar equivalents of base, still more preferably between about 50 and about 1000 molar equivalents of base, and yet still more preferably between about 100 and about 400 molar equivalents of base are used (relative to Group 8, 9, or 10 metal).

The carbonylation reaction can be carried out in a batch reactor or a continuous or semi-continuous reactor system comprising one or more reaction vessels. Reaction vessels suitable for use in the process according to the invention with either homogeneous or heterogeneous catalysts include stirrer vessels, autoclaves and bubble columns, it being possible for these to be employed as individual reactors or as a cascade. In a cascade 2 to 15, preferably 2 to 10, and particularly preferably 2 to 5, reactors may be connected in series.

Due in part to the low solubility of carbon monoxide in organic hydroxy compounds, such as phenol, it is preferable that a reactor vessel be pressurized. The composition of the reaction gases carbon monoxide and oxygen can be varied in broad concentration ranges. Preferably a carbon monoxide oxygen molar ratio (normalized on carbon monoxide) of 1:(0.001–1.0) is employed, more preferably 1:(0.01–0.5) and still more preferably 1:(0.02–0.3). A total pressure in the range of between about 0.1013–50.6625 megapascals, preferably about 0.3447–25.33 megapascals, more preferably about 1.013–17.2369 megapascals, and yet still more preferably about 1.013–15.1987 megapascals is typically used.

The reaction gases are not subject to special purity requirements but care must be taken to ensure that no catalyst poisons such as sulfur or compounds thereof are introduced. In the preferred embodiment of the process according to the invention, pure carbon monoxide and pure oxygen are used. Carbon monoxide and oxygen can be introduced as a mixture or in a preferred embodiment of the process according to the invention, carbon monoxide and oxygen may be added independently of each other. When a reactor cascade is used instead of an individual reactor, the separate oxygen addition preferably proceeds in such a way that the optimal oxygen concentration is ensured in each of the reactors.

The carbon monoxide may be high-purity carbon monoxide or carbon monoxide diluted with another gas which has no negative effects on the reaction, such as nitrogen, noble gases, argon, or carbon dioxide. The oxygen used in the present invention may be high purity oxygen, air, or oxygen diluted with any other gas which has no negative effects on the reaction, such as nitrogen, noble gases, argon, or carbon dioxide. The concentration of inert gas in the reaction gas may amount to 0 to about 60 volume %, Cu(II) acetlylacetonate, titanium as titanium (IV) oxide acetylacetonate, sodium bromide, sodium hydroxide and tetraglyme (6–12 wt. %) under a gas mixture containing 9 mole % oxygen in carbon monoxide at 10.342 megapascals. Reaction mixtures also contained a desiccant (30 grams $\frac{1}{16}$ inch 3A molecular sieves) contained in perforated TEFLON basket mounted on the stir shaft. Reaction was carried out in a batch-batch regime in that no additional gas mixture was supplied unless indicated otherwise. For each reaction, data listed was for point of maximum DPC yield over 2.5 hours. DPC and bromophenols are reported as weight % of the total reaction mixture.

TABLE I

| Example | Pd ppm | Cu eq. vs. Pd | Ti eq. vs. Pd | NaOH eq. vs. Pd | NaBr eq. vs. Pd | Tetraglyme wt. % | DPC wt. % | Pd TON | Bromophenols wt. % | Selectivity, % |
|---|---|---|---|---|---|---|---|---|---|---|
| 1 | 24 | 10 | 15 | 278 | 775 | 12 | 27.6 | 5917 | 0.65 | 76.4 |
| 2 | 24 | 4 | 14 | 275 | 783 | 12 | 25.1 | 5421 | 0.73 | 78.7 |
| 3 | 14 | 5 | 15 | 341 | 748 | 6 | 23.5 | 8779 | 0.60 | 81.9 |
| 4 | 13 | 8 | 10 | 201 | 402 | 6 | 20.7 | 8095 | 0.27 | 83.2 |
| 5 | 13 | 5 | 5 | 475 | 400 | 6 | 17.8 | 7030 | 0.22 | 80.7 |
| 6 | 13 | 21 | 21 | 1127 | 477 | 7 | 27.2 | 10570 | 0.12 | 78.9 |
| 7[a] | 13 | 13 | 25 | 482 | 321 | 7 | 25.4 | 9747 | 0.31 | 81.1 |
| 8[b] | 14 | 12 | 24 | 225 | 450 | 7 | 23.6 | 8378 | 0.31 | 79.0 |

Amounts are in ppm (parts per million) or equivalents (eq).
[a]Reaction was carried out in a batch-flow regime - gas mixture passed through liquid phase at the rate 300 standard cubic centimeters per minute
[b]Reaction used palladium nitrate hydrate preferably 0 to about 20, and more preferably 0 to about 5 volume %. The concentration of 0 volume % represents the special case of the preferred state which is free of inert gas.

Provision may be made for including a drying agent or a drying process step in the reaction. For example, drying agents, typically molecular sieves, may be present in the reaction vessel. Reaction temperatures in the range of between about 50° C. and about 150° C. are preferred. Gas sparging or mixing can be used to aid the reaction.

The following examples are included to provide additional guidance to those skilled in the art in practicing the claimed invention. While some of the examples are illustrative of various embodiments of the claimed invention, others are comparative. The examples provided are merely representative of the work that contributes to the teaching of the present application. Accordingly, these examples are not intended to limit the invention, as defined in the appended claims, in any manner.

As discussed supra, the economics of aromatic carbonate production is dependent on the number of moles of aromatic carbonate produced per mole of Group 8, 9, or 10 metal utilized. In the following examples, the aromatic carbonate produced is diphenylcarbonate (DPC) and the Group 8, 9, or 10 metal utilized is palladium. For convenience, the number of moles of DPC produced per mole of palladium charged to a reactor is referred to as the palladium turnover number (Pd TON). Selectivity to DPC was calculated as 0.5 moles DPC produced/(moles phenol charged—moles phenol remaining). Another useful metric was the ratio of DPC (a desired product) to bromophenols (undesired byproducts).

EXAMPLES 1–8

Reaction mixtures contained 60–62 grams phenol; palladium as Pd(II) acetylacetonate or Pd(II) nitrate; copper as

EXAMPLES 9–18

Diphenyl carbonate was produced in a glass reaction vessel containing 0.15 millimolar concentration of palladium (II) acetylacetonate in phenol, various equivalents of sodium hydroxide, various equivalents of sodium bromide, various volume % amounts of tetraglyme, and various IOCC combinations in diverse amounts. Titanium was supplied as titanium (IV) oxide acetylacetonate and copper as copper (II) acetylacetonate. The components were heated to 100° C. for 3 hours in an atmosphere of approximately 6–7 mole % oxygen in carbon monoxide at about 11.03 megapascals. Average results of multiple runs are given in Table II.

TABLE II

| Example | Cu eq.vs.Pd | Ti eq.vs.Pd | NaOH eq.vs.Pd | tetraglyme vol % | NaBr eq.vs.Pd | avg. Pd TON |
|---|---|---|---|---|---|---|
| 9 | 4 | 20 | 500 | 12 | 599 | 6901 |
| 10 | 20 | 20 | 500 | 12 | 200 | 6645 |
| 11 | 20 | 10 | 500 | 9.3 | 400 | 6595 |
| 12 | 12 | 40 | 500 | 12 | 200 | 6569 |
| 13 | 4 | 40 | 500 | 8.0 | 200 | 6289 |
| 14 | 4 | 10 | 500 | 12 | 200 | 6198 |
| 15 | 12 | 25 | 350 | 7.9 | 484 | 6010 |
| 16 | 4 | 10 | 350 | 8.0 | 200 | 5997 |
| 17 | 4 | 10 | 500 | 7.5 | 800 | 5977 |
| 18 | 20 | 30 | 500 | 12 | 599 | 5960 |

It will be understood that each of the elements d scribed above, or two or more together, may also find utility in applications differing from the types described herein. While the invention has been illustrated and described as embodied in a method and catalyst system for producing aromatic carbonates, it is not intended to be limited to the details shown, since various modifications and substitutions can be made without departing in any way from the spirit of the present invention. For example additional effective IOCC compounds can be added to the reaction. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A carbonylation catalyst system, comprising
   at least one Group 8, 9, or 10 metal source;
   at least one bromide composition;
   at least one organic solvent;
   a combination of inorganic co-catalysts comprising at least one titanium source and at least one copper source; and
   at least one base.

2. The carbonylation catalyst system of claim 1, wherein the Group 8, 9, or 10 metal source is a palladium source.

3. The carbonylation catalyst system of claim 2, wherein the palladium source is a palladium(II) salt or complex.

4. The carbonylation catalyst system of claim 3, wherein the palladium source is palladium acetylacetonate.

5. The carbonylation catalyst system of claim 2, wherein the palladium source is palladium metal supported on an inorganic or organic support.

6. The carbonylation catalyst system of claim 5, wherein the palladium source is palladium on carbon.

7. The carbonylation catalyst system of claim 1, wherein the bromide composition is an alkali metal bromide salt.

8. The carbonylation catalyst system of claim 1, wherein the organic solvent is a polyether.

9. The carbonylation catalyst system of claim 1, wherein the organic solvent is a nitrile.

10. The carbonylation catalyst system of claim 1, wherein the organic solvent is a carboxylic acid amide.

11. The carbonylation catalyst system of claim 1, wherein the organic solvent is a sulfone.

12. The carbonylation catalyst system of claim 2, wherein the molar ratio of titanium relative to palladium is between about 0.1 and about 150.

13. The carbonylation catalyst system of claim 2, wherein the molar ratio of copper relative to palladium is between about 0.1 and about 15.

14. A carbonylation catalyst system, comprising
    a Group 8, 9, or 10 metal source;
    a bromide composition;
    a polyether;
    a combination of inorganic co-catalysts comprising a titanium source and a copper source; and a base.

15. The carbonylation catalyst system of claim 14, wherein the Group 8, 9, or 10 metal source is a palladium source.

16. The carbonylation catalyst system of claim 15, wherein the palladium source is a palladium(II) salt or complex.

17. The carbonylation catalyst system of claim 16, wherein the palladium source is palladium acetylacetonate.

18. The carbonylation catalyst system of claim 14, wherein the bromide composition is an alkali metal bromide salt.

19. The carbonylation catalyst system of claim 15, wherein the molar ratio of titanium relative to palladium is between about 0.1 and about 150.

20. The carbonylation catalyst system of claim 15, wherein the molar ratio of copper relative to palladium is between about 0.1 and about 15.

21. A carbonylation catalyst system, comprising a palladium source;
    an alkali metal bromide salt;
    tetraglyme;
    a combination of inorganic co-catalysts comprising a titanium source and a copper source; and
    a base.

22. The carbonylation catalyst system of claim 21, wherein the alkali metal bromide salt is sodium bromide.

23. A carbonylation catalyst system for carbonylating aromatic hydroxy compounds, comprising
    at least one Group 8, 9, or 10 metal source;
    at least one bromide composition;
    at least one organic solvent;
    a combination of inorganic co-catalysts comprising at least one titanium source and at least one copper source; and
    at least one base;
    wherein the Group 8, 9, or 10 metal source s present in an amount of about 1 mole of metal per 800–1,000,000 moles of aromatic hydroxy compound; the bromide composition is present in an amount of between about 1 and about 2000 moles of, bromide per mole of the Group 8, 9, or 10 metal source; the organic solvent is present in an amount of about 1–60% by volume, based on the total of aromatic hydroxy compound and organic solvent; at least one inorganic co-catalyst is present in the amount of about 0.2–200 gram-atoms of metals per gram-atom of the Group 8, 9, or 10 metal; and base is present in an amount of between about 0.1 and about 2500 molar equivalents relative to Group 8, 9, or 10 metal.

24. The carbonylation catalyst system of claim 23, wherein the Group 8, 9, or 10 metal source is a palladium source.

25. The carbonylation catalyst system of claim 23, wherein the bromide composition is an alkali metal bromide salt.

26. The carbonylation catalyst system of claim 25, wherein the alkali metal bromide salt is sodium bromide.

27. The carbonylation catalyst system of claim 23 wherein the organic solvent is at least one member selected from the group consisting of a polyether, a nitrile, a carboxylic acid amide, and a sulfone.

28. The carbonylation catalyst system of claim 27 wherein the organic solvent is tetraglyme.

29. The carbonylation catalyst system of claim 24, wherein the molar ratio of titanium relative to palladium is between about 0.1 and about 150.

30. The carbonylation catalyst of claim 24, wherein the molar ratio of copper relative to palladium is between about 0.1 and about 15.

* * * * *